United States Patent [19]

Petzoldt et al.

[11] Patent Number: 5,250,712
[45] Date of Patent: Oct. 5, 1993

[54] 1β,15α-DIHYDROXY-1α-METHYL-5α-ANDROSTANE-3,17-DIONE, ITS PRODUCTION AND USE

[75] Inventors: Karl Petzoldt; Helmut Hofmeister, both of Berlin, Fed. Rep. of Germany

[73] Assignee: Schering Aktiengesellschaft, Berlin and Bergkamen, Fed. Rep. of Germany

[21] Appl. No.: 902,567

[22] Filed: Jun. 22, 1992

Related U.S. Application Data

[63] Continuation of Ser. No. 459,697, filed as PCT/DE89/00362, May 30, 1989, published as WO89/12064, Dec. 14, 1989, abandoned.

[30] Foreign Application Priority Data

May 30, 1988 [DE] Fed. Rep. of Germany ....... 3818747

[51] Int. Cl.$^5$ .............................................. C07J 1/00
[52] U.S. Cl. .................................................. 552/613
[58] Field of Search ...................................... 552/613

[56] References Cited

PUBLICATIONS

Jones, Tetrahedron 42:3351–3403 (1986).

*Primary Examiner*—Marianne M. Cintins
*Assistant Examiner*—Kimberly J. Kestler
*Attorney, Agent, or Firm*—Millen, White, Zelano & Branigan

[57] ABSTRACT

The invention relates to the 1β, 15α-dihydroxy-1α-methyl-5α-androstane-3,17-dione of formula I

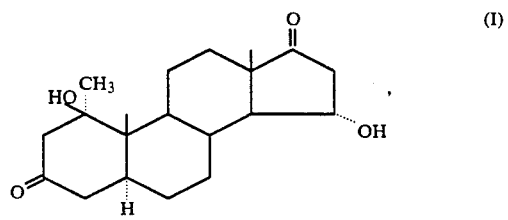

and preparation thereof using microorganisms of the genera Glomerella or Fusarium. The invention also relates to further processing of the compound of formula I to obtain pharmacologically effective steroids.

1 Claim, No Drawings

1β,15α-DIHYDROXY-1α-METHYL-5α-ANDROSTANE-3,17-DIONE, ITS PRODUCTION AND USE

This application is a continuation of application Ser. No. 07/459,697, filed as PCT/DE89/00362, May 30, 1989, published as WO89/12064, Dec. 14, 1989, now abandoned.

SUMMARY OF THE INVENTION

The invention relates to 1β, 15α-dihydroxy-1alpha-methyl-5α-androstane-3,17-dione of formula I

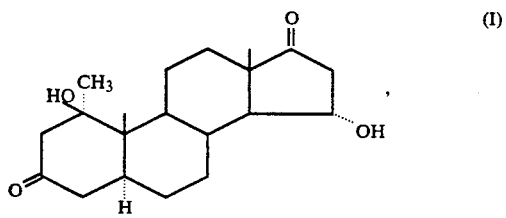

Further, the invention relates to a process for the production of 1β,15α-dihydroxy-1α-methyl-5α-androstane-3,17-dione, which is characterized in that 1α-methyl-5α-androstane-3,17-dione of formula II

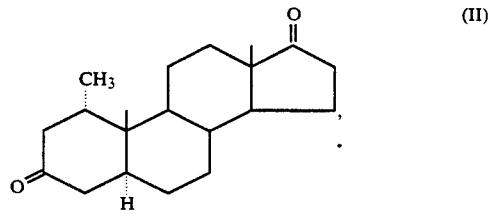

is fermented with a culture of a microorganism of the genus Glomerella or Fusarium.

By the term "microorganism of the genus Glomerella or Fusarium" are to be understood according to the invention as those microorganisms which are deposited with recognized depositories under said generic names and are freely available to experts. In the experiments conducted so far, 5 species of these genera were examined for their ability to perform the process according to the invention, of which *Glomerella Cingulata* (ATCC 10534) and *Fusarium oxysporum* (ATCC 7808) proved particularly suitable. According to available studies, the process according to the invention can also be performed quite well with the use of microorganisms of the species *Glomerella fusaroides* (ATCC 9552) and *Glumerella glycines* (ATCC 11871).

The process according to the invention is performed under the same fermentation conditions that are used in the known microbiological hydroxylations of steroids with these microorganisms.

Submerged cultures are cultivated under culture conditions usually used for these microorganisms in a suitable nutrient medium with aeration. Then the substrate is added to the cultures (dissolved in a suitable solvent or in emulsified form) and fermented until a maximum substrate conversion is reached.

Suitable substrate solvents are, for example, methanol, ethanol, glycolmonomethyl ether, dimethylformamide or dimethyl sulfoxide. Emulsification of the substrate can be performed, for example, by the latter being sprayed in micronized form or in a water-miscible solvent (such as methanol, ethanol, acetone, glycolmonomethyl ether, dimethylformamide or dimethyl sulfoxide) with strong turbulence in (preferably decalcified) water, which contains the usual emulsification auxiliary agents. Suitable emulsification auxiliary agents are nonionogenic emulsifiers, such as, for example, ethylenoxy adducts or fatty acid esters of polyglycols. As suitable emulsifiers there can be mentioned, for example, the commercially available wetting agents Tegin ®, Tween ® and Span ®.

The optimal substrate concentration, substrate addition time and fermentation period depends on the type of microorganism used and the fermentation conditions. These magnitudes, as generally necessary in microbiological steroid conversions, must be determined in individual cases by pretesting, as is familiar to one skilled in the art.

The 1α-methyl-5α-androstane-3,17-dione, used as starting material for the process according to the invention, is already known (see DE-A-25 58 089). In can be prepared in a simple way by oxidation of mesterolone.

It is very surprising for one skilled in the art that with the help of the process according to the invention it is possible to prepare 1β, 15α-dihydroxy-1α-methyl-5α-androstane-3,17-dione in yields of about 75% of theory. This is surprising because as a rule saturated steroids are only very unsatisfactorily hydroxylated, isolated keto groups are mostly reduced and a 1-methyl group present in the steroid molecule generally proves to be troublesome.

The 1β,15α-dihydroxy-1α-methyl-5α-androstane-3,17-dione according to the invention is a valuable intermediate product, which makes it possible to synthesize numerous pharmacologically effective steroids substituted in the 15 position in a considerably simpler way than is possible according to the previously known processes.

Such pharmacologically effective steroids are, for example, the 1β,15α-alkyl-1-methyl-1,4-androstadiene-3,17-diones known from EP-A 86730177.2 and the 1-methyl-(1-oxyalkyl)-1,4-androstadiene-3,17-diones described in EP-A 88101991.3.

Important intermediate products for the production of these compounds are androstane derivatives of general formula III

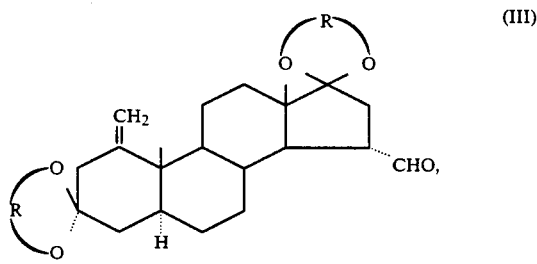

in which

R each represents an alkylene group with 2 to 6 carbon atoms. This invention also relates to these androstane derivatives of general formula III.

Finally, the invention relates to a process for the production of these androstane derivatives, which is characterized in that the 15α hydroxy group of the 1β,15α-dihydroxy-1α-methyl-5α-androstane-3,17-dione produced according to claim 1 is exchanged for a cyanide group, water is cleaved from the 15β-cyano-1β-hydroxy-1α-methyl-5α-androstane-3,17-dione thus prepared, the resulting 15β-cyano-1-methyl-5α-androst-1-ene-3,17-dione is ketalized with an alkane diol containing 2 to 6 carbon atoms, and the resultant cyano compound of general formula IV

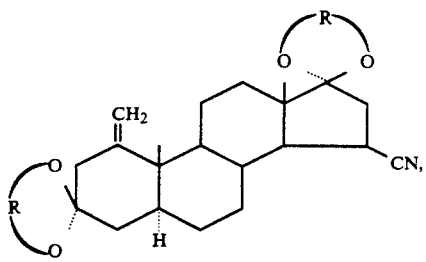

in which

R has the above-named meaning is partially reduced.
The resulting mixture of isomeric aldehydes is isomerized with bases to the 15α-aldehydes of general formula III.

The conversion of the 1β,15α-dihydroxy-1α-methyl-5α-androstane-3,17-dione into the 15β,cyano-1β-hydroxy-1α-methyl-5α-androstane-3,17-dione can be performed simply, for example, by the 15-hydroxy group being esterified (for example, with acetic anhydride or acetyl chloride) and the ester radical is exchanged for the cyano group.

This is surprising for one skilled in the art, since it is known that in general it is not possible to arrive at the cyanides corresponding to the alcohol radical directly from esters of organic acids (Methoden der Organischen Chemie [Methods of Organic Chemistry] (Houben-Weyl, George Thieme Verlag, Stuttgart, Germany), 4th ed., vol. VIII, 1952, p. 288).

The resulting 15β-cyano-1β-hydroxy-12α-methyl-5α-androstane-3,17-dione can be dehydrated in the in the usual way as expected; thus, for example, by the action of dehydrating agents on this compound. Also conventional is the ketalization of the formed 15β-cyano-1-methyl-5α-androst-1-ene-3,17-dione by means of alkane diols containing 2 to 6 carbon atoms (such as, for example, 1,2-ethanediol, 1,3-propanediol, 2,2-dimethyl-1,3-propanediol or 2,3-butanediol) in the presence of dehydrating agents (such as, for example, ortho esters) and acids or lewis acids.

Surprisingly, is not necessary to isomerize the formed 15β-cyano compounds by bases to isolate the 15α-cyano compounds from the isomeric mixture—which is quite expensive—and to reduce the latter partially, but the 15β-cyano compounds can be partially reduced directly (for example, with complex metal hydrides such as diisobutyl-aluminum hydride) and the resulting isomeric mixture of 17α and 17β formyl compounds can surprisingly be rearranged with bases practically completely to the desired 17α-formyl compounds of general formula III.

The further conversion of the aldehydes of general formula III into pharmacologically effective steroids can be performed analogously to those conversions already known 17β-hydroxy-1α-methyl-3α-(2-tetrahydropyranyloxy)-5α-androstane-15α-carboxaldehyde (see the above-mentioned European patent applications).

The following embodiment examples serve for detailed explanation of the process according to the invention and the usability of the process products.

A. Embodiment examples relating to the processes according to the invention

EXAMPLE 1

A 2-liter Erlenmeyer flask, which is filled with 500 ml of a nutrient medium, sterilized for 30 minutes at 120° C. in an autoclave and containing

| 3.0% | glucose |
|---|---|
| 1.0% | cornsteep liquor |
| 0.2% | sodium nitrate |
| 0.1% | potassium dihydrogenphosphate |
| 0.2% | dipotassium hydrogenphosphate |
| 0.05% | magnesium sulfate heptahydrate |
| 0.002% | iron(II) sulfate heptahydrate and |
| 0.05% | potassium chloride | is inoculated with a slant tube culture of the strain Glomevella cingulata (ATCC 10534) and shaken for 48 hours at 28° C. on a rotary shaker (165 revolutions per minute).

A 20-liter prefermenter is inoculated with 250 ml of this growth culture and filled with 15 liters of a sterilized medium of the same composition as the growth culture at 121° C. and 1.1 bars of excess pressure. It is germinated for 24 hours with addition of silicon SH as an antifoaming agent at 29° C. and 0.7 bar of excess pressure with aeration (15 liters per minute) and stirring (220 revolutions per minute).

Then 3 liters of this culture is removed under sterile conditions and is used to inoculate a 75-liter main fermenter, which is charged with 47 liters of a nutrient medium, sterilized as above, containing

| 1.0% | glucose |
|---|---|
| 1.0% | cornsteep liquor |
| 0.2% | sodium nitrate |
| 0.1% | potassium dihydrogenphosphate |
| 0.2% | dipotassium hydrogenphosphate |
| 0.05% | magnesium sulfate heptahydrate |
| 0.002% | iron(II) sulfate heptahydrate and |
| 0.05% | potassium chloride |

After a growth phase of 12 hours under prefermenter conditions, a sterilized solution of 20 g of 1α-methyl-5α-androstane-3,17-dione in 350 ml of dimethylformamide is added and further stirred and aerated. After 38 hours of contact time, the culture broth is extracted twice with 25 liters of methyl isobutyl ketone each, and the extracts are combined and evaporated to dryness in a vacuum. The residue is taken up in methanol, the undissolved remaining silicone oil (antifoaming agent) is filtered off and evaporation to dryness is again performed. The oily crystalline residue is recrystallized from acetone, the crystallizate is washed again with cold acetone and dried in a vacuum drying cabinet. 17.3 g of 1β, 15α-dihydroxy-1α-methyl-5α-androstane-3,17-dione with a melting point of 227° to 229° C. is obtained.

EXAMPLE 2

Two 2-liter Erlenmeyer flasks each of which is filled with 500 ml of a nutrient medium, sterilized for 30 minutes at 120° C. and containing

| 3.0% | glucose |
|---|---|
| 1.0% | cornsteep liquor |
| 0.2% | sodium nitrate |
| 0.1% | potassium dihydrogenphosphate |
| 0.2% | dipotassium hydrogenphosphate |
| 0.05% | magnesium sulfate heptahydrate |
| 0.002% | iron(II) sulfate heptahydrate and |

| | |
|---|---|
| -continued | |
| 0.05% | potassium chloride | each is inoculated with a slant tube culture of the strain Fusarium Oxysporum (ATCC 7808) and shaken for 48 hours at 28° C. on a rotary shaker.

A 30-liter fermenter is inoculated with the contents of the two growth flasks and charged with 19 liters of a sterilized medium of the same composition as the growth culture for 60 minutes at 121° C. and 1.1 bars of excess pressure. With addition of silicone SH as antifoaming agent, the contents are germinated at 29° C. and 0.7 bar of excess pressure under aeration (20 liters per minute) and stirring (220 revolutions per minute) and after 12 hours of growth time the substrate in the form of a solution of 8 g of 1α-methyl-5α-androstane-3,17-dione in 135 ml of dimethylformamide, sterilized by filtering, is added. The conversion is terminated after another 86 hours of stirring and aeration. The culture broth is extracted twice with 10 liters of methyl isobutyl ketone each, the extracts are combined and evaporated to dryness in a vacuum. The remaining residue is dissolved in methanol for removal of the silicone oil and the undissolved remaining antifoaming agent is filtered off by a double folded filter. The methanol solution is again brought to dryness after treatment with activated carbon and the residue is recrystallized from acetone. After the crystallizate is suctioned off and drying in a vacuum drying cabinet 6.1 g of 1β,15α-dihydroxy-1α-methyl-5α-androstane-3,17-dione with a melting point of 225°–227° C. is obtained.

EXAMPLE 3

20 ml of acetic anhydride is instilled at room temperature in 10.0 g of 1β,15α-dihydroxy-1α-methyl-5α-androstane-3,17-dione in 40 ml of pyridine. The reaction mixture is stirred into ice/water after 2.5 hours. The precipitated product is suctioned off, dissolved in ethyl acetate and washed neutral with water. The crude product is chromatographed on silica gel with a hexane-ethyl acetate gradient. 8.6 g of 15α-acetoxy-1β-hydroxy-1α-methyl-5α-androstane-3,17-dione is obtained. Melting point 170.0° C.

b) 21.3 g of 15α-acetoxy-1β-hydroxy-1α-methyl-5α-androstane-3,17-dione is reacted in 146 ml of tetrahydrofuran and 15 ml of water with vigorous stirring with 10.7 g of potassium cyanide at 80° C. After 20 hours the reaction mixture is concentrated by evaporation to half and stirred into ice/water. The precipitated product is suctioned off, dissolved in dichloromethane and washed neutral with water. The crude product is chromatographed on silica gel with a methylene chloride-acetone gradient. Yield 15β-cyano-1β-hydroxy-1α-methyl-5α-androstane-3,17-dione. Melting point 224° C.

c) 2.0 g of 15β-cyano-1β-hydroxy-1α-methyl-5α-androstane-3,17-dione is stirred in 20 ml of glacial acetic acid with 6 ml of trifluoroacetic anhydride at room temperature. After 4 hours the solution is added to ice/water. The precipitated product is suctioned off, dissolved in ethyl acetate and washed with water. 1.7 g of 15β-cyano-1-methyl-5α-androst-1-ene-3,17-dione with a melting point of 193° C. is obtained.

d) 1.4 g of 15β-cyano-1-methyl-15α-androst-1-ene-3,17-dione in 14 ml of dichloromethane is reacted with 14 ml of 1,2-ethanediol, 5 ml of trimethylorthoformiate and 25 mg of p-toluenesulfonic acid at 50° C. After 24 hours the solution is mixed with 2 ml of pyridine and largely concentrated by evaporation in a vacuum. The residue is stirred into ice/water. The precipitated product is suctioned off, dissolved in ethyl acetate and washed with water. After chromatographing of the crude product on silica gel with a hexane-ethyl acetate gradient, 1.2 g of 3,3;17,17-bis(ethylenedioxy)-1-methylene-5α-androstane-15β-carbonitrile with a melting point of 229° C. is obtained.

e) 180 ml of a 1.2 molar solution of diisobutylaluminum hydride in toluene is instilled in 44.0 g of 3,3;17,17-bis(ethylenedioxy)-1-methylene-5α-androstane-15beta-carbonitrile in 700 ml of toluene at −30° C. under argon. After 1 hour, about 300 ml of 10% aqueous tartaric acid solution is slowly added at −30° C. Then it is diluted with ethyl acetate, another 100 ml of 10% tartaric solution is added and stirred at room temperature. After 30 minutes the organic phase is washed neutral with sodium bicarbonate solution and water saturated with sodium chloride. The crude product is chromatographed on silica gel with hexane-ethyl acetate gradient. 27.5 g of 3,3;17,17-bis(ethylenedioxy)-1-methylene-5α-androstane-15α and 15β-carbaldehyde is isolated as isomeric mixture.

f) 27.5 g of 3,3;17,17-bis(ethylenedioxy)-1-methylene-5α-androstane-15α and 15β-carbonitrile is stirred at room temperature in 100 ml of methylene chloride with 75 ml of 1 N methanolic potassium hydroxide solution. After 20 hours, it is mixed with methylene chloride and washed neutral with water. 27.0 g of 3,3;17,17-bis(ethylenedioxy)-1-methylene-5α-androstane-15α-carbaldehyde is obtained. Melting point 192° C. (from acetone/hexane).

B. Embodiment example relating to further processing of the process products a) 3.8 g of 3,3;17,17-bis(ethylenedioxy)-1-methylene-5α-androstane-15α-carbaldehyde in 46 ml of dimethylformamide is stirred under argon with 3.0 g of trimethylsulfonium iodide and 2.3 g of potassium tert-butylate at room temperature. After 30 minutes the reaction mixture is added to ice/water. The precipitated product is suctioned off, dissolved in dichloromethane, washed neutral with water. 3.5 g of 3,3;17,17-bis(ethylenedioxy)-1-methylene-15α-(2-oxiranyl)5α-androstane is obtained as foam.

b) 4.3 g of 3,3;17,17-bis(ethylenedioxy)-1-methylene1-5α-(2-oxiranyl)-5α-androstane in 100 ml of methanol is stirred with 5.8 g of sodium methylate under reflux. The precipitated product is suctioned off, dissolved in dichloromethane and washed neutral with water. 4.0 g of 3,3;17,17-bis(ethylenedioxy)-15α-(1R-hydroxy-2-methoxyethyl)-1-methylene-5α-androstane is obtained as oily product.

c) 3.5 g of 3,3;17,17-bis(ethylenedioxy)-15α-(1R-hydroxy-2-methoxy-ethyl)-1-methylene-5α-androstane is reacted in 14 ml of pyridine with 70 ml of acetic anhydride at room temperature. After 6 hours the solution is added to ice/water. The precipitated product is suctioned off, dissolved in dichloromethane and washed with water. 3.1 g of 15α-(1R-acetoxy-2-methoxy-ethyl)-3,3;17,17-bis(ethylenedioxy)-1-methylene-5α-androstane is obtained as foam.

d) 2.9 g of 15α-(1R-acetoxy-2methoxy-ethyl) 3,3;17,17-bis(ethylenedioxy)-1-methylene-5α-androstane in 30 ml of methanol and 6 ml of water is stirred with 2.9 g of oxalic acid under reflux. After 1 hour the reaction mixture is concentrated by evaporation in a vacuum and stirred into ice/water. The precipitated product is suctioned off and washed neutral with water.

1.6 g of 15α-(1R-acetoxy-2-methoxy-ethyl)-1-methyl-5α-androst-1-ene-3,17-dione with a melting point of 190° C. is obtained.

e) 1.2 g of 15α-(1R-acetoxy-2-methoxy-ethyl)-1-methyl-5α-androst-1-ene-3,17-dione in 40 ml of dioxane is stirred at 80° C. with 1.2 g of 2,3-dichloro-5,6-dicyano-p-benzoquinone. After 7 hours the mixture is allowed to cool, is filtered, the filtrate is diluted with ethyl acetate and washed several times with sodium bicarbonate solution and water. The crude product is chromatographed on silica gel with a methylene chloride-acetone gradient. Yield: 780 mg of 15α-(1R-acetoxy-2-methoxy-ethyl)-1-methyl-1,4-methyl-androstadiene-3,17-dione. Melting point 184° C. (from acetone/isopropyl ether).

The compound thus prepared is pharmacologically effective. Pharmaceutical preparations which contain this compound are suitable, i.a., for treatment of estrogen-induced or stimulated tumors (breast cancer, prostatic hyperplasia) and for influencing fertility (EP-A 88 101 991.3).

We claim:

1. 1β,15α-Dihydroxy-1α-methyl-5α-androstane-3,17-dione of formula I

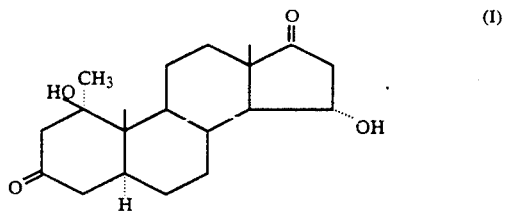

* * * * *